(12) United States Patent
Steinberg et al.

(10) Patent No.: US 10,201,553 B1
(45) Date of Patent: Feb. 12, 2019

(54) COMPOSITION OF NATURAL PRODUCTS FOR IMPROVED BRAIN FUNCTIONING

(71) Applicant: H Smart Inc., Bonsall, CA (US)

(72) Inventors: Dianna Steinberg, Fallbrook, CA (US); Tim Altvater, Pala, CA (US)

(73) Assignee: H Smart Inc., Bonsall, CA (US)

( * ) Notice: Subject to any disclaimer, the term of this patent is extended or adjusted under 35 U.S.C. 154(b) by 77 days.

(21) Appl. No.: 15/651,648

(22) Filed: Jul. 17, 2017

Related U.S. Application Data

(60) Provisional application No. 62/363,527, filed on Jul. 18, 2016.

(51) Int. Cl.
| | | |
|---|---|---|
| *A61K 36/00* | (2006.01) |
| *A61K 31/685* | (2006.01) |
| *A61K 31/05* | (2006.01) |
| *A61K 31/047* | (2006.01) |
| *A61K 31/683* | (2006.01) |
| *A61K 47/36* | (2006.01) |
| *A61K 9/00* | (2006.01) |
| *A61K 9/20* | (2006.01) |
| *A61K 9/48* | (2006.01) |
| *A61K 47/40* | (2006.01) |
| *A61K 47/12* | (2006.01) |
| *A61K 45/06* | (2006.01) |

(52) U.S. Cl.
CPC .......... *A61K 31/685* (2013.01); *A61K 9/0053* (2013.01); *A61K 9/20* (2013.01); *A61K 9/205* (2013.01); *A61K 9/2013* (2013.01); *A61K 9/48* (2013.01); *A61K 9/4858* (2013.01); *A61K 9/4866* (2013.01); *A61K 31/047* (2013.01); *A61K 31/05* (2013.01); *A61K 31/683* (2013.01); *A61K 45/06* (2013.01); *A61K 47/12* (2013.01); *A61K 47/36* (2013.01); *A61K 47/40* (2013.01)

(58) Field of Classification Search
CPC ...................................................... A61K 36/00
USPC ........................................................ 424/725
See application file for complete search history.

(56) References Cited

U.S. PATENT DOCUMENTS 8,980,907 B2 *  3/2015  Baker, Jr. ............. A61K 47/595
                                                           514/282

* cited by examiner

*Primary Examiner* — Michael V Meller
(74) *Attorney, Agent, or Firm* — Levisohn Berger LLP

(57) ABSTRACT

A pharmaceutical composition for the prevention, protective effect, or treatment of a neurodegenerative condition, is provided. The composition includes a combination of cannabidiol water soluble powder; astaxanthin; alpha-glyceryl phosphoryl choline; and phosphatidyl serine. Optional supporting ingredients may be provided also.

1 Claim, No Drawings

COMPOSITION OF NATURAL PRODUCTS FOR IMPROVED BRAIN FUNCTIONING

CROSS REFERENCE TO RELATED PATENT APPLICATION

This patent application claims priority to U.S. Provisional Patent Application No. 62/363,527, filed Jul. 18, 2016, the entire contents of which are incorporated by reference.

BACKGROUND

The increasing incidence of neurologic and neurodegenerative disease has prompted a surge in scientific research on prevention and/or reversal of brain and nervous system pathology (i.e. mood disorders, memory loss, seizures, difficulty concentrating, insomnia, ADD, Alzheimer's, autism, traumatic brain injury, dementia, "brain fog," post-concussion syndrome, migraines, neuropathy, MS, Parkinson's).

Pharmaceutical intervention has been of limited benefit for patients with neurological pathology, while often causing troublesome side effects.

A variety of natural products have been shown, in clinical trials, to improve neurological and cognitive functioning. Several product formulations have been marketed recently to improve brain function. The efficacy of some of these blends approaches that of the standard pharmaceutical drugs.

The present invention is unique in that this product utilizes a synergistic blend of natural neuroprotective and neuroregenerative compounds, including cannabidiol (CBD), all in clinically researched and verified therapeutic amounts. Clinical studies indicate that CBD facilitates brain recovery from oxidative stress, free radical damage and inflammation.

CBD research is extensive and compelling. The brain is "hardwired" with specialized receptors for CBD. Each ingredient in this invention has been clinically validated to provide a specific neuro-protective or neuro-regenerative effect. This unique formulation promises to revolutionize the safe and effective optimization of brain and neurological function.

SUMMARY OF THE INVENTION

The core ingredients for this invention are CBD, astaxanthin, phosphoryl choline and phosphatidyl serine which together promote and support neurogenesis and have neuroprotective effects.

In an embodiment, a synergistic composition is provided with the following formula:

| CORE INGREDIENTS | |
|---|---|
| CBD (Cannabidiol) Water Soluble Powder | 5 mg to 20 mg |
| Astaxanthin | 2 mg to 12 mg |
| Alpha-Glyceryl Phosphoryl choline | 100 mg to 600 mg |
| Phosphatidyl Serine | 100 mg to 600 mg |

In an embodiment, the amount of water soluble CBD in the composition is 5 mg or 10 mg. In an embodiment, the amount of astaxanthin is 2 mg, the amount of alpha-glyceryl phosphoryl choline is 100 mg, and the amount of Phosphatidyl Serine is 100 mg.

In an embodiment, the following additional ingredients are provided in the composition:

| SUPPORTING INGREDIENTS | |
|---|---|
| Vitamin D-3 | 800 IU |
| Vitamin B6 | 20 mg |
| Vitamin B12 (as Methlycobalamin) | 2.4 mcg |
| Vitamin B9 (as Folate) | 300 mcg |
| Ashwaganda | 125 mg |
| Bacopa | 300 mg |
| Piperine (Black Pepper Extract) | 5 mg |
| Huperzia Serrata (Huperzine-A 200 mcg yield) | 20 mg |
| Green Tea Extract (EGCG 80%) | 100 mg |
| L-Theanine 98% (from Green Tea) | 100 mg |
| Rhodiola Rosea Extract Rosavins 3% + Salidroside 2% | 200 mg |
| Tumeric Complex (4:1 Concentrate) | 100 mg |
| Trace Minerals (72 Mineral Blend) | 50 mg |
| Vinpocetine 99% | 20 mg |

In an embodiment, the composition is provided as a tablet or capsule. In an embodiment, the composition may be formulated with one or more excipients, such as binders, lubricants, fillers (diluents), disintegrating agents, lubricants, and glidants. Approved FD&C and D&C dyes or lakes, flavors, and sweetening agents also may be present.

DETAILED DESCRIPTION

This invention provides pharmaceutical compositions that prevent, exert a protective effect, and treat the effects of neurogenerative condition with a novel combination of ingredients that have synergistic beneficial effects.

As used herein, neurodegenerative conditions that may be beneficially prevented, protected, or treated include mood disorders, memory loss, seizures, difficulty concentrating, insomnia, ADD, autism, traumatic brain injury, "brain fog," post-concussion syndrome, migraine headaches, neuropathy, multiple sclerosis, and degenerative disorders such as Parkinson's Disease, Alzheimer's Disease, other dementia disorders.

As used herein, "prevention" means administering the pharmaceutical composition to a person with no neurological impairment, who is at risk for neurological impairment, to prevent the onset of a neurodegenerative condition.

As used herein, "exerting a protective effective" means arresting or slowing the progression of a progressive neurogenerative disease, such as Alzheimer's Disease or Parkinson's Disease.

This invention includes a set of core ingredients plus a set of supporting ingredients that in combination are believed to exert a synergistic effect.

Core Ingredients
Cannabidiol (CBD)

Nearly every health challenge has, at its foundation, inflammation and oxidative stress. Recent discovery of the complexities of the body's intrinsic endocannabinoid system shows promise in the prevention and amelioration of inflammatory disorders. Evidence shows CBD to be a safe and effective compound that may alleviate inflammation and the free radical damage of oxidative stress.

Cannabidiol is one of at least 113 active cannabinoids identified in *cannabis*. It is a major phytocannabinoid, accounting for up to 40% of the plant's extract. CBD is considered to have a wide scope of potential medical applications—due to clinical reports showing the lack of side effects, particularly a lack of psychoactivity (as is typically associated with Δ9-THC), and non-interference with several psychomotor learning and psychological functions.

Cannabidiol has been shown to reverse cognitive defects in mice and to exert neuroprotective, anti-oxidative, and anti-inflammatory properties in vitro and in vivo. A key study demonstrated a decrease in neuroinflammation and dietary phytosterol retention. This study provides evidence that CBD may have potential for preventative treatment for the symptoms of social withdrawal and impaired facial recognition. (J Alzheimers Dis. 2014; 42(4): 1383-96.)

The endocanabinoid system (ECS) is involved with neuroprotection, neurogenesis, synaptic plasticity, regulation of motor activity, immune modulation, inflammation, pain, memory processing, and brain ageing. This research has identified the role of phytocanabinnoid compounds in targeting the ECS for the treatment of neurodegeneration, pain and mood disturbance. (Philos Trans R Soc Lon B Biol Sci 2012 Dec. 5; 367(1607):3193-200)

Cannabinoids also may attenuate the effects of ageing upon neuroinflammation and may stimulate neurogenesis. (Neurobiol Dis. 2009 May; 34(2): 300-7). Cannabidiol possesses neuroprotective characteristics that are promising for clinical use. (Eur J Neurosci. 2013 November: 38(10): 3424-34. Epub 2013 Aug. 25.)

In the inventive composition, the CBD is part of a hemp oil extract that contains naturally occurring CBD, terpenes, and other phytocannabinoids. In an embodiment, the hemp oil extract is emulsified with a material such as lecithin, a surfactant such as polysorbate 20, gum arabic, or similar ingredient with similar properties. In an embodiment, gum arabic is used as the emulsifying agent.

In an embodiment, the hemp oil extract is blended with the emulsifying agent in water to form a colloid that is dried to give a free-flowing powder emulsion. In an embodiment, specialized processing equipment is used to emulsify the hemp extract to give particle sizes that can range from 50 nm to 250 nm depending on application requirements for enhanced bio-availability. The emulsified hemp oil extract is believed to have greater water solubility and better bioavailability than native hemp oil. The free-flowing powder is easily blended with other ingredients for packing into capsules or pressing into tablets.

Astaxanthin

Oxidative stress and inflammation are widely recognized as contributing to neurological and cognitive impairment. Astaxanthin (AstaReal) is a potent antioxidant that also exhibits anti-inflammatory properties. Studies have shown that natural astaxanthin reduces oxidative stress and inflammation, improves lipid profiles, promotes better blood flow in capillaries, and lowers blood pressure in hypertensive individuals. Importantly, no adverse effects have been reported in these studies. A large body of clinical and experimental research strongly suggests that astaxanthin can contribute to improved brain health.

Brain specialists have started to pay close attention to the preventive and therapeutic effects of micronutrients on brain health such as natural astaxanthin. Randomized double-blind, placebo-controlled studies have shown that 3-months supplementation of natural astaxanthin improve mental quickness, multitasking, memory and faster learning in senior subjects complaining of age-related forgetfulness and loss of mental sharpness.

Clinical studies also suggest that astaxanthin may fight vascular dementia by reducing oxidative by-products in red blood cells and promoting collective improvements of the blood lipid profile, blood antioxidant capacity, capillary blood flow and blood pressure. A large body of scientific research as well as testimonial evidence suggests that astaxanthin can improve subjects' information-processing, memory and learning and support brain function. See, for example, Hussein G et al., (2005). Biol Pharm Bull. January; 28 (1):47-52. Astaxanthin may be beneficial for preventing neurotoxicity (Mar Drugs. 2016 March: 14(3). Epub 2016 Mar. 10.). Astaxanthin supplementation was also shown to enhance neurogenesis and spatial memory in mice (Mol Nutr Food Res 2015 Dec. 8).

Alpha-Glyceryl Phosphoryl Choline

L-alpha glyceryl phosphoryl choline (Alpha-GPC), is a precursor to the neurotransmitter acetylcholine and is also converted to phosphatidylcholine after oral ingestion, is naturally present in almost every cell membrane in the body. A decline in acetylcholine levels coincides with advancing age and is a hallmark of neurodegeneration.

Studies suggest that alpha-GPC is useful in improving cognitive function in impaired individuals. De Jesus Moreno Moreno M (January 2003). "Cognitive improvement in mild to moderate Alzheimer's dementia after treatment with the acetylcholine precursor choline alfoscerate: a multicenter, double-blind, randomized, placebo-controlled trial". Clin Ther. 25 (1): 178-93. PMID 12637119. doi:10.1016/S0149-2918(03)90023-3. See also Doggrell SA & Evans S; Evans (October 2003). "Treatment of dementia with neurotransmission modulation". Expert Opin. Investig. Drugs, 12 (10): 1633-1654. PMID 14519085, doi:10.1517/13543784.12.10.1633. Alpha-GPC may therefore improve brain functions, including memory, concentration, learning, recall, and focus.

Alpha-GPC may also promote formation of acetylcholine (AC), a vital neurotransmitter compound involved in all key brain functions and mental sharpness. Alpha-GPC may help speed cell to cell communication through neuromuscular optimization, providing enhanced muscular power output and agility for active and athletic individuals. Alpha-GPC may also enhance the physiological production and maintenance of human growth hormone, which decreases with age.

Dosages of 100 mg to 600 mg are clinically supported. A commercial form of this ingredient is sold under the tradename ALPHASIZE®.

Phosphatidylserine

Phosphatidylserine (PS) is required for normal cellular structure and function. Brain tissues are especially rich in phosphatidylserine, but aging causes a decline in the PS content of cells throughout the body.

Research has shown that in addition to improving neural function, PS enhances energy metabolism in all cells, memory, concentration, learning and word choice. In the brain, PS helps maintain cell membrane integrity and brain-cell-to-brain-cell connections.

Additionally, phosphatidylserine helps the brain use its fuel efficiently. By boosting glucose metabolism and stimulating production of acetylcholine, supplemental phosphatidylserine has been shown to improve the condition of patients experiencing age-associated memory impairment or cognitive decline.

Supporting Ingredients

Vitamin B6

Vitamin B6 is believed to assist in the production of neurotransmitters, the chemicals that allow brain and nerve cells to communicate with one another. Vitamin B6 is often used, along with folate and vitamin B12, to treat high homocysteine levels. Elevated homocysteine levels (hyperhomocysteinemia) makes a person more prone to endothelial cell injury, which leads to inflammation in the blood vessels, which in turn may lead to atherogenesis, which can result in ischemic injury. Memory loss, difficulty concentrating, and mood disorders may also be improved via vitamin B6 supplementation. One clinical study demonstrated a marked reduction in seizures with high dose B6. (Brain Dev. 1987; 9(4); 418-21.). It has also been suggested that vitamin B6 may be useful in the treatment of autism. (Magnes Res. 2006 March; 19(1): 53-62.)

Vitamin B9 (L-Methylfolate)

Folate is essential for brain development and function. Low folate levels, with resulting high homocysteine concentrations, are associated with cognitive dysfunction. Supplementation with bio-active folate has been shown to improve memory by reducing oxidative stress and maintaining integrity of neurons during aging. (Cell Mol Neurobiol. 2011 January; 31(1): 83-91.)

Vitamin B12 (Methylcobalamin)

Vitamin B12 is essential for the preservation of the myelin sheath around neurons and for the synthesis of neurotransmitters. The bio-active form of vitamin B12 is methylcobalamin. Clinical studies demonstrate that B12 works synergistically with vitamin B6 and folate to slow cognitive decline, reduce homocysteine levels, and improve migraine symptoms. (Pharmacogenet Genomics. 2009 June; 19(6): 422-8.; C. A. de Jager, et al., "Cognitive and clinical outcomes of homocysteine-lowering B-vitamin treatment in mild cognitive impairment: a randomized controlled trial," Int J Geriatr Psychiatry. 2012 June; 27(6):592-600. doi: 10.1002/gps.2758. Epub 2011 Jul. 21.)

Vitamin D3

In humans, poor vitamin D dietary intake and low serum vitamin D3 levels have been linked to cognitive decline and degenerative brain disease in the elderly. Several clinical studies have found an association between low serum D3 levels and significant cognitive impairment. Vitamin D3 has also been shown to down-regulate inflammation and to stimulate the clearance of beta amyloid plaques from the brain. A. Masoumi, et al. J Alzheimers Dis. 2009 July; 17 (3); 703-17 doi: 10.3233/JAD-2009-1080; S. Tarbali, Iran J Basic Med Sci. 2016 January; 19 (1); 80-8.; OK Danner, et al., J Nutr Metab. 2016; 2016:4280876; Junyan Feng, et al. "Clinical improvement following vitamin D3 supplementation in Autism Spectrum Disorder" Nutritional Neuroscience Vol. 20, Iss. 5, 2017, doi: 10.1080/1028415X.2015.1123847.

Ashwagandha

Ashwagandha is an Ayurvedic herb with restorative properties. It is believed to provide multiple health benefits in stress reduction, increased energy, mental acuity and concentration.

Research suggests that ashwagandha confers neuroprotection by supporting the regeneration of axons and dendrites, nerve cell components that support brain and nervous system function. Ashwagandha also inhibits an enzyme (acetylcholinesterase) that breaks down acetylcholine in the brain. By preserving acetylcholine, ashwagandha helps to maintain youthful cognition and memory.

Bacopa

Bacopa is an ayurvedic herb that has been shown to have nootropic effects. A standardized formulation, BACOGNIZE®, is available commercially. L Hingorani, S Patel, B Ebersole, Sustained cognitive effects and safety of HPLC-standardized Bacopa Monnieri extract: A randomized, placebo controlled clinical trial, Planta Med 2012; 78-PH22, DOI: 10.1055/s-0032-1320681

Piperine

Piperine is an alkaloid that is partially responsible for the pungency of black pepper. It is also referred to as black pepper extract. Piperine is believed to have medicinal effects, including modulating efflux mechanisms, modulating metabolic enzymes, and stimulating thermogenesis, the metabolic process that generates energy at the cellular level. Thermogenesis has been identified as playing an integral role in utilizing the daily food and nutrients that the human body consumes. It sets in motion the mechanisms that lead to digestion and subsequent gastrointestinal absorption.

The thermogenic effect increases thermal energy sufficient to "power up" the mechanism related to thermogenesis. This in turn results in increased metabolic processes that creates a demand for the supply of a broad range of nutrients that contribute to metabolism, i.e. vitamins, minerals, herbals, amino acids, etc. This provides a more efficient mode of nutrient transportation into the blood.

A standardized piperine extract is commercially available under the tradename BIOPERINE®.

*Huperzia serrata*

An extract from the plant commonly known as northern firmoss (*Huperzia serrata*), Huperzine A is a naturally derived acetylcholinesterase inhibitor. Acetylcholinesterase (AchE) is responsible for the breakdown of Acetylcholine, and so by inhibiting AchE, more acetylcholine is made available to the brain.

Huperzine A is used for Alzheimer's disease, memory and learning enhancement, and age-related memory impairment. It is also used for increasing alertness and energy.

Green Tea Extract

A recent report found that green tea extract increases the brain's effective connectivity, meaning the causal influence that one brain area exerts over another. This effect on connectivity also led to improvement in actual cognitive performance: Subjects tested significantly better for working memory tasks after the admission of green tea extract. Schmidt, A., H et al. "Green tea extract enhances parieto-frontal connectivity during working memory processing," Psychopharmacology (2014) 231: 3879. doi:10.1007/s00213-014-3526-1

L-Theanine

L-Theanine is the predominant amino acid of tea that produces calming effects in the brain by increasing levels of serotonin and dopamine, and blocking the binding of L-glutamic acid to glutamate receptors. The calming, mood-enhancing effect is achieved by helping to increase alpha-brain waves, electrical brain activity commonly present when a person is very relaxed and in a good mood.

Just as meditation, massage or aromatherapy quiets the mind and body, theanine plays a role in inducing the same calm and feeling of well-being without drowsiness. It is a non-toxic, highly desirable mood modulator.

A standardized formulation is commercially available under the tradename SUNTHEANINE®. A dosage of 100 mg is typical.

*Rhodiola rosea* Extract

The Russian herb rhodiola (*Rhodiola rosea*, Rosavins 3%+Salidroside 2%) is remarkable in its ability to support cellular energy metabolism by promoting higher levels of ATP (adenosine triphosphate) and CP (creatine phosphate) in the mitochondria. In a human clinical trial, *rhodiola* aided exercise endurance after just a single dose. In a double-blind crossover human trial, *rhodiola* increased several measures of mental performance, including associative thinking, short-term memory, concentration, calculation and speed of audio/visual perception. Statistically significant improvements were reported after just two weeks of supplementation. More recent clinical trials have found that *Rhodiola rosea* significantly improves physical and cognitive function.

Trace Minerals (72 Mineral Blend)

Trace minerals are well known as vital nutrients. In particular, magnesium is a critical mineral that participates in more than 300 metabolic reactions, many of which are needed for normal brain function. A 72-mineral blend, including a beneficial quantity of magnesium, obtained from the Great Salt Lake in Utah provides a standardized form of this blend, sold under the brand name CONCENTRACE®.

Turmeric

Clinical research has shown that curcumin, a constituent of whole turmeric, may help inhibit the accumulation of destructive beta-amyloids in the brain. Recent animal research suggests another bioactive compound in turmeric called aromatic-turmerone can increase neural stem cell growth in the brain by as much as 80 percent. Neural stem cells differentiate into neurons and play an important role in brain repair. Cells bathed in the turmeric compound also appeared to specialize into certain types of brain cells more rapidly. These findings suggest that whole turmeric may help in the recovery of brain function in neurodegenerative situations. J Alzheimers Dis. 2006 September; 10 (1); 1-7; J Neurochem. 2007 August; 102(4):1095-104. Epub 2007 Apr. 30; Ayu. 2012 October; 33 (4): 499-504; J Alzheimers Dis. 2009 July; 17 (3):703-17; Neuroreport. 2010 Nov. 24; Neurochem Int. 2009 March-April; 54(3-4); 199-204.

Vinpocetine 99%

Vinpocetine enhances cerebral circulation. In adults, cerebral blood flow is typically 750 milliliters per minute or 15% of the cardiac output. An extract of the periwinkle plant, vinpocetine enhances cerebral metabolism by helping to maintain healthy blood flow and oxygen utilization. Szilagyi, G. Z. et al., "Effects of vinpocetine on the redistribution of cerebral blood flow and glucose metabolism in chronic ischemic stroke patients: A PET study" Journal of the Neurological Sciences. 229-230: 275-284 (2005), PMID 15760651. doi:10.1016/j.jns.2004.11.053; Dézsi, L., et al., "Neuroprotective effects of vinpocetine in vivo and in vitro. Apovincaminic acid derivatives as potential therapeutic tools in ischemic stroke". Acta pharmaceutica Hungarica. 72 (2): 84-91 (2002). PMID 12498034.

Pharmaceutical Compositions

In an embodiment, the composition is provided as a tablet or capsule that may be manufactured by any technique known in the art for manufacturing oral dosage forms. In an embodiment, the composition may be formulated with one or more excipients, such as binders, lubricants, fillers (diluents), disintegrating agents, lubricants, and glidants. Approved FD&C and D&C dyes or lakes, flavors, and sweetening agents also may be present.

For example, tablet formulations may be manufactured by a granulation process, wherein the ingredients are blended to form a granulate that can be compressed into tablets in a tablet press.

In an embodiment, the pharmaceutical composition is provided as a capsule. In a capsule formulation, typically the ingredients and at least one excipient are blended into a free-flowing powder that is packed into a capsule shell. For example, the capsule may be a two-piece shell, in which the male half is packed with the composition in a capsulation machine, and then the female half is mated to the male half. The capsule may be a hard gelatin capsule. In a capsule formulation, it is usually important that the contents form a free-flowing powder. Desiccating agents typically aid this process. In an embodiment, maltodextrin and magnesium stearate are added to the composition, which aid in achieving the correct bulk quantity and in providing a powder that can be efficiently and consistently packed into capsules.

In the instant composition, the CBD material is provided as a free-flowing powder as a result of the emulsification process employed. Maltodextrin, if present, also aids in providing a free-flowing powder for packing into capsules.

It should be understood that the preferred embodiment was described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly legally and equitably entitled.

The invention claimed is:

1. A tablet or capsule for treatment of a neurodegenerative condition in a human in need thereof consisting essentially of therapeutically effective amounts of cannabidiol, astaxanthin, alpha-glyceryl phosphoryl choline, phosphatidyl serine, Vitamin B12, Ashwaganda, Bacopa, piperine, Huperzia *Serrata*, Green Tea Extract, L-Theanine, *Rhodiola Rosea* Extract, magnesium mineral, and turmeric.

\* \* \* \* \*